US00PP23129P2

(12) United States Plant Patent
Page

(10) Patent No.: US PP23,129 P2
(45) Date of Patent: Oct. 23, 2012

(54) ***FILIPENDULA* PLANT NAMED 'WBPREST'**

(50) Latin Name: ***Filipendula multijuga*×*Filipendula palmata***
Varietal Denomination: Wbprest

(75) Inventor: Stephen Page, Oude Wetering (NL)

(73) Assignee: Specialis Plants BV, Oude Wetering (NL)

( * ) Notice: Subject to any disclaimer, the term of this patent is extended or adjusted under 35 U.S.C. 154(b) by 0 days.

(21) Appl. No.: 13/135,603

(22) Filed: Jul. 8, 2011

(51) Int. Cl.
*A01H 5/00* (2006.01)

(52) U.S. Cl. ..... Plt./226

(58) Field of Classification Search ..... Plt./226, Plt./263.1
See application file for complete search history.

*Primary Examiner* — Kent L Bell
(74) *Attorney, Agent, or Firm* — C. A. Whealy

(57) ABSTRACT

A new and distinct cultivar of *Filipendula* plant named 'Wbprest', characterized by its compact, upright, broadly outwardly spreading and mounding plant habit; freely branching habit; green-colored leaves with dark greyed purple-colored venation; numerous light red purple-colored flowers; good garden performance; and low temperature hardiness.

2 Drawing Sheets

Botanical designation: *Filipendula multijuga*×*Filipendula palmata.*

Cultivar denomination: 'WBPREST'.

BACKGROUND OF THE INVENTION

The present invention relates to a new and distinct cultivar of *Filipendula* plant, botanically known as *Filipendula multijuga*×*Filipendula palmata* and hereinafter referred to by the name 'Wbprest'.

The new *Filipendula* plant is a product of a planned breeding program conducted by the Inventor in Hillegom, The Netherlands. The objective of the breeding program is to develop new compact and freely flowering *Filipendula* plants with attractive foliage and flowers.

The new *Filipendula* plant originated from a cross-pollination conducted by the Inventor during the summer of 2003 of a proprietary selection of *Filipendula multijuga*, not patented, as the female, or seed, parent with a proprietary selection of *Filipendula palmata*, not patented, as the male, or pollen, parent. The new *Filipendula* plant was discovered and selected by the Inventor in July, 2005 as a single flowering plant within the progeny of the stated cross-pollination in a controlled environment in Hillegom, The Netherlands.

Asexual reproduction of the new *Filipendula* plant by divisions and by micro propagation in a controlled greenhouse environment in Hillegom, The Netherlands since February, 2006 has shown that the unique features of this new *Filipendula* plant are stable and reproduced true to type in successive generations of asexual reproduction.

SUMMARY OF THE INVENTION

Plants of the new *Filipendula* have not been observed under all possible environmental conditions and various cultural practices. The phenotype may vary somewhat with variations in environment such as temperature and light intensity without, however, any variance in genotype.

The following traits have been repeatedly observed and are determined to be the unique characteristics of 'Wbprest'.

These characteristics in combination distinguish 'Wbprest' as a new and distinct *Filipendula* plant:

1. Compact, upright, broadly outwardly spreading and mounding plant habit.
2. Freely branching habit.
3. Green-colored leaves with dark greyed purple-colored venation.
4. Numerous light red purple-colored flowers.
5. Good garden performance and hardy to low temperatures.

Plants of the new *Filipendula* can be compared to plants of the female parent selection. Plants of the new *Filipendula* differ from plants of the female parent selection in the following characteristics:

1. Plants of the new *Filipendula* are shorter than plants of the female parent selection.
2. Leaves of plants of the new *Filipendula* and the female parent selection differ in color as leaves of plants of the female parent selection have green-colored venation.
3. Flowers of plants of the new *Filipendula* are lighter in color than flowers of plants of the female parent selection.

Plants of the new *Filipendula* can be compared to plants of the male parent selection. Plants of the new *Filipendula* differ from plants of the male parent selection in the following characteristics:

1. Plants of the new *Filipendula* are shorter than plants of the male parent selection.
2. Leaves of plants of the new *Filipendula* and the male parent selection differ in color as leaves of plants of the male parent selection have green-colored venation.
3. Flowers of plants of the new *Filipendula* are lighter in color than flowers of plants of the male parent selection.

Plants of the new *Filipendula* can be compared to plants of *Filipendula purpurea* 'Kahome', not patented. Plants of the new *Filipendula* differ from plants of 'Kahome' in the following characteristics:

1. Plants of the new *Filipendula* are shorter than plants of 'Kahome'.

2. Leaves of plants of the new *Filipendula* and 'Kahome' differ in color as leaves of plants of 'Kahome' have green-colored venation.
3. Flowers of plants of the new *Filipendula* are lighter in color than flowers of plants of 'Kahome'.

Plants of the new *Filipendula* can also be compared to plants of *Filipendula palmata* 'Nana', not patented. Plants of the new *Filipendula* differ from plants of 'Nana' in the following characteristics:

1. Plants of the new *Filipendula* are taller than plants of 'Nana'.
2. Leaves of plants of the new *Filipendula* and 'Nana' differ in color as leaves of plants of 'Nana' have green-colored venation.
3. Flowers of plants of the new *Filipendula* are lighter in color than flowers of plants of 'Nana'.

BRIEF DESCRIPTION OF THE PHOTOGRAPHS

The accompanying colored photographs illustrate the overall appearance of the new *Filipendula* plant showing the colors as true as it is reasonably possible to obtain in colored reproductions of this type. Colors in the photographs may differ slightly from the color values cited in the detailed botanical description which accurately describe the colors of the new *Filipendula* plant.

The photograph on the first sheet is a side perspective view of a typical plant of 'Wbprest' grown in an outdoor nursery.

The photograph at the bottom of the second sheet is a close-up view of typical leaves of 'Wbprest'.

The photograph at the top of the second sheet is a close-up view of typical inflorescences of 'Wbprest'.

DETAILED BOTANICAL DESCRIPTION

The aforementioned photographs and following observations, measurements and values describe plants of the new *Filipendula* grown during the late spring in ground beds in an outdoor nursery in Hillegom, The Netherlands and under cultural conditions which closely approximate commercial *Filipendula* production. During the production of the plants, day temperatures ranged from 14° C. to 28° C. and night temperatures ranged from 4° C. to 18° C. Plants were three years old when the photographs and the description were taken. In the following description, color references are made to The Royal Horticultural Society Colour Chart, 2007 Edition, except where general terms of ordinary dictionary significance are used.

Botanical classification: *Filipendula multijuga*×*Filipendula palmata* 'Wbprest'.

Parentage:

*Female, or seed, parent*.—Proprietary selection of *Filipendula multijuga*, not patented.

*Male, or pollen, parent*.—Proprietary selection of *Filipendula palmata*, not patented.

Propagation:

*Type*.—By micro-propagation.

*Time to initiate roots, summer*.—About eight to ten days at 20° C.

*Time to initiate roots, winter*.—About 21 to 24 days at 10° C.

*Time to produce a rooted young plant, summer*.—About eight weeks at 15° C.

*Time to produce a rooted young plant, winter*.—About twelve weeks at 12° C.

*Root description*.—Medium in thickness, fibrous; brown in color.

*Rooting habit*.—Freely branching; dense.

Plant description:

*Plant form and growth habit*.—Perennial shrub; compact, upright, broadly outwardly spreading and mounding plant habit; moderately vigorous growth habit.

*Branching habit*.—Freely branching habit with about 25 basal lateral branches; pinching (removal of terminal apices) is not required.

*Plant height*.—About 66.5 cm.

*Plant diameter* (*area of spread*).—About 103 cm.

Lateral branch description:

*Length*.—About 53.7 cm.

*Diameter*.—About 3 mm.

*Internode length*.—About 6.3 cm.

*Strength*.—Strong.

*Aspect*.—About 30° from vertical.

*Texture*.—Smooth, glabrous.

*Color*.—Close to 144B.

Foliage description:

*Arrangement*.—Alternate, simple.

*Length*.—About 12.1 cm.

*Width*.—About 12.8 cm.

*Shape*.—Palmately lobed.

*Apex*.—Narrowly acute.

*Base*.—Hastate, not overlapping.

*Margin*.—Bi-serrate.

*Texture, upper surface*.—Smooth, glabrous.

*Texture, lower surface*.—Smooth; veins, moderately pubescent.

*Venation pattern*.—Palmate.

*Color*.—Developing leaves, upper surface: Close to N137B. Developing leaves, lower surface: Close to 137C. Fully expanded leaves, upper surface: Darker than between N137C and 143A; venation, close to N186C. Fully expanded leaves, lower surface: Close to 147B; venation, between 182C and 183D.

*Petiole*.—Length: About 12.4 cm. Diameter: About 2 mm. Texture, upper and lower surfaces: Smooth, glabrous. Color, upper surface: Close to 152B to 152C. Color, lower surface: Close to 144B.

*Stipules*.—Length: About 1.8 cm. Width: About 9 mm. Shape: Obovate. Apex: Acute. Color, upper and lower surfaces: Close to 144B to 144C.

Flower description:

*Flower appearance/arrangement*.—Single rotate flowers arranged in terminal and axillary branched umbels; freely flowering habit with usually about 350 flowers per terminal inflorescence and about 150 flowers per axillary inflorescence; flowers face upright to outwardly.

*Natural flowering season*.—Plants begin flowering about ten months after planting; flowering continuous from the late spring through the summer in The Netherlands.

*Flower longevity*.—Flowers last about ten days on the plant; flowers not persistent.

*Fragrance*.—Faintly fragrant; sweet and fresh.

*Inflorescence height*.—About 8.3 cm.

*Inflorescence diameter*.—About 9.7 cm.

*Flower diameter*.—About 1 cm.

*Flower length* (*height*).—About 7 mm.

*Flower bud*.—Length: About 2 mm. Diameter: About 2 mm. Shape: Globular. Color: Close to 60D; towards the base, close to 146A and 195D.

*Petals*.—Quantity per flower: Single whorl of five. Length: About 2.5 mm. Width: About 2 mm. Shape: Broadly obovate; concave. Apex: Obtuse. Margin: Entire. Texture, upper and lower surfaces: Smooth, glabrous. Color: When opening, upper and lower surfaces: Close to 68A to 68B; towards the base, close to 62C. Fully opened, upper and lower surfaces: Close to 68B to 68C.

*Sepals*.—Quantity per flower: Single whorl of four; calyx campanulate. Length: About 1.5 mm. Width: About 1 mm. Shape: Ovate. Apex: Broadly acute. Base: Fused. Margin: Entire. Texture, upper and lower surfaces: Smooth, glabrous. Color: When opening, upper and lower surfaces: Close to 146A and 195D. Fully opened, upper surface: Towards the base, close to 70C to 70D; towards the apex, close to 146A. Fully opened, lower surface: Towards the base, close to 70D; towards the apex, close to 146A.

*Peduncles*.—Length: About 17.4 cm. Diameter: About 1.5 mm. Strength: Strong. Aspect: Terminal inflorescences, erect; axillary inflorescences, about 40° from vertical. Texture: Smooth, glabrous. Color, upper surface: Close to 176A; distally, strongly tinged with close to 183B. Color, lower surface: Close to 146D; distally, tinged with close to 184B.

*Pedicels*.—Length: About 1 mm. Diameter: About 0.3 mm. Strength: Moderately strong. Aspect: About 45° from peduncle axis. Texture: Smooth, glabrous. Color: Between 183B and 184B.

*Reproductive organs*.—Androecium: Quantity per flower: About 50. Filament length: About 3.5 mm. Filament color: Close to 186D. Anther shape: Broadly ovate, basifixed. Anther length: About 0.2 mm. Anther color: Close to 185B. Amount of pollen: Scarce. Pollen color: Close to 155A. Gynoecium: Quantity per flower: Seven. Pistil length: About 1 mm. Style length: About 0.6 mm. Style color: Close to 64B. Stigma appearance: Club-shaped. Stigma color: Close to 155A. Ovary color: Close to 64A to 64B.

*Seeds and fruits*.—Seed and fruit development has not been observed on plants of the new *Filipendula*.

Garden performance: Plants of the new *Filipendula* have been observed to have good garden performance and to tolerate rain, wind and high temperatures of about 35° C. and to be hardy to USDA Hardiness Zone 4.

Pathogen/pest resistance: Plants of the new *Filipendula* have not been observed to be resistant to pathogens and pests common to *Filipendula*.

It is claimed:

1. A new and distinct *Filipendula* plant named 'Wbprest' as illustrated and described.

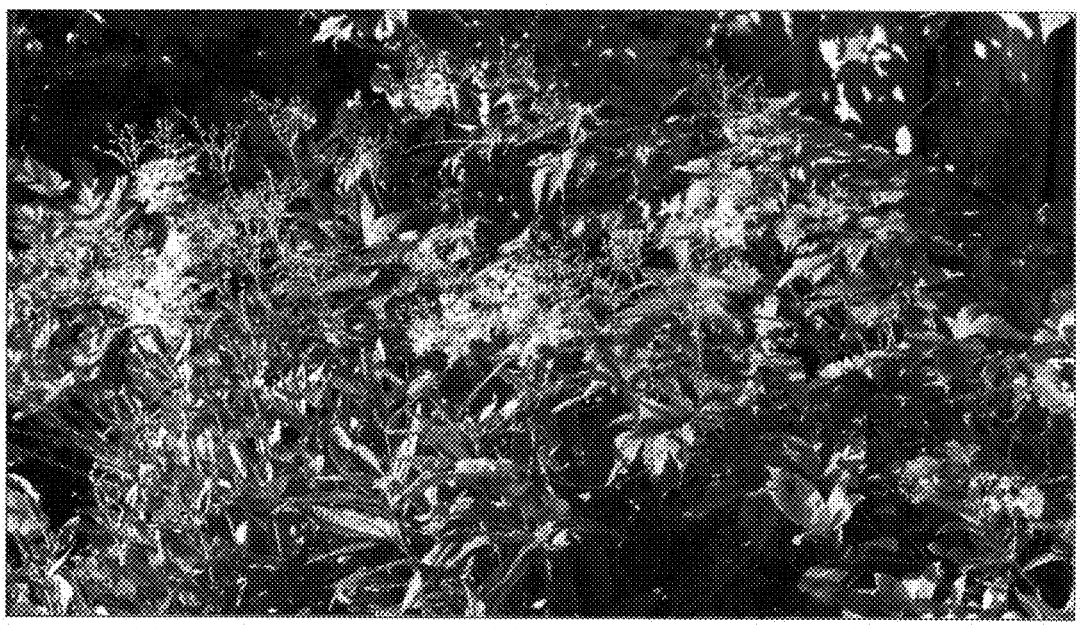

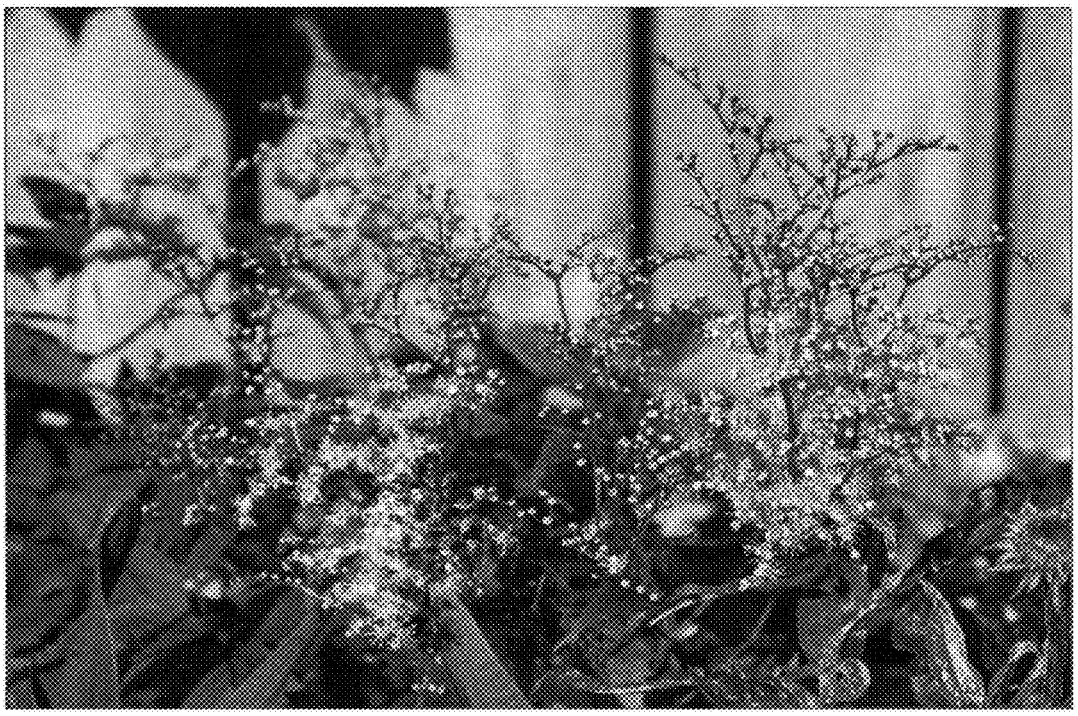
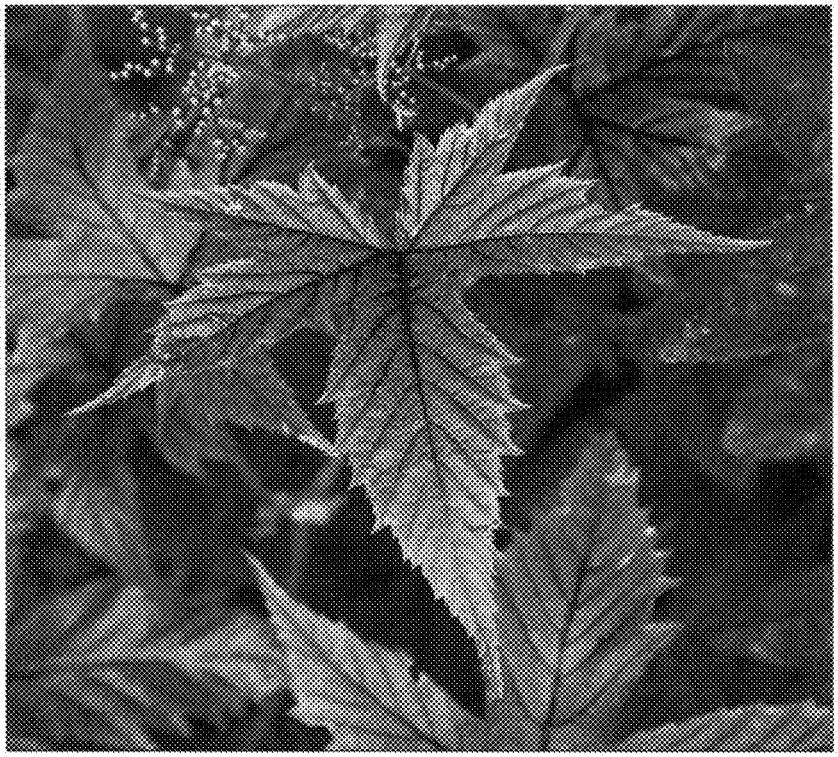

* * * * *